(12) United States Patent
Lombari et al.

(10) Patent No.: US 7,108,015 B2
(45) Date of Patent: Sep. 19, 2006

(54) IN-LINE FLOW THROUGH DIAPHRAGM TANK

(75) Inventors: Robert Lombari, North Smithfield, RI (US); Wei-Chiao Lo, Taichung (TW)

(73) Assignee: Flexcon Industries, Randolph, MA (US)

( * ) Notice: Subject to any disclaimer, the term of this patent is extended or adjusted under 35 U.S.C. 154(b) by 0 days.

(21) Appl. No.: 10/626,079

(22) Filed: Jul. 24, 2003

(65) Prior Publication Data

US 2005/0034774 A1 Feb. 17, 2005

Related U.S. Application Data

(63) Continuation-in-part of application No. 10/281,708, filed on Oct. 28, 2002, now abandoned.

(60) Provisional application No. 60/398,765, filed on Jul. 25, 2002.

(51) Int. Cl.
*F16L 55/04* (2006.01)

(52) U.S. Cl. .............................. 138/30; 138/26; 138/42; 220/720; 220/721; 220/723

(58) Field of Classification Search .................. 138/30, 138/26, 31; 220/720, 721, 723
See application file for complete search history.

(56) References Cited

U.S. PATENT DOCUMENTS

| | | | | |
|---|---|---|---|---|
| 2,609,001 A | * | 9/1952 | Hebard ......................... | 138/30 |
| 2,841,181 A | | 7/1958 | Hewitt et al. .................. | 138/30 |
| 3,063,470 A | | 11/1962 | Forster ......................... | 138/30 |
| 3,536,102 A | * | 10/1970 | Zahid et al. ................... | 138/30 |
| 4,088,154 A | | 5/1978 | Patton et al. .................. | 138/30 |
| 4,263,498 A | | 4/1981 | Meyers ......................... | 219/312 |
| 4,628,964 A | | 12/1986 | Sugimura et al. ............. | 138/30 |
| 4,705,077 A | | 11/1987 | Sugimura ...................... | 138/30 |
| 4,732,175 A | | 3/1988 | Pareja ........................... | 138/30 |
| 4,732,176 A | | 3/1988 | Sugimura ...................... | 138/30 |
| 4,759,387 A | | 7/1988 | Arendt .......................... | 138/30 |
| 4,784,181 A | | 11/1988 | Hilverdink .................... | 138/30 |
| 5,027,860 A | | 7/1991 | Tuthill, Jr. ..................... | 138/30 |
| 5,386,925 A | | 2/1995 | Lane ............................. | 220/530 |
| 5,584,316 A | | 12/1996 | Lund ............................ | 137/337 |
| 5,690,061 A | | 11/1997 | Lopez ........................... | 122/17 |
| 5,732,741 A | | 3/1998 | Shiery .......................... | 138/30 |
| 5,735,313 A | | 4/1998 | Jenski et al. .................. | 138/30 |
| 5,823,007 A | | 10/1998 | Chang .......................... | 62/397 |
| 5,860,452 A | | 1/1999 | Ellis ............................. | 138/30 |
| 5,988,984 A | | 11/1999 | Austin ....................... | 417/44.2 |
| 6,041,820 A | | 3/2000 | Boehme ....................... | 138/30 |
| 6,063,275 A | | 5/2000 | Traylor ......................... | 210/248 |

(Continued)

FOREIGN PATENT DOCUMENTS

DE 8203569 9/1982

(Continued)

OTHER PUBLICATIONS

AQUA-STOR, Water Storage Units for 6" & 6-1/2" Wells, 4' & 8' Models, data sheet, Dempster Industries, Inc., dated before Jul. 24, 2003 (1 pg.).

(Continued)

*Primary Examiner*—Patrick Brinson
(74) *Attorney, Agent, or Firm*—Valerie B. Rosen; Choate, Hall & Stewart, LLP

(57) ABSTRACT

An in-line expansion tank. As fluid traverses a pipe within the tank, it may pass into and displace a diaphragm disposed outside of the pipe if the fluid pressure is greater than a tank pressure pushing the diaphragm against the pipe. When the fluid pressure decreases, the fluid passes from the diaphragm back into the pipe.

28 Claims, 6 Drawing Sheets

U.S. PATENT DOCUMENTS

| | | | |
|---|---|---|---|
| 6,264,247 B1 | 7/2001 | Lombari et al. | 285/202 |
| 6,328,071 B1 | 12/2001 | Austin | 138/30 |
| 6,418,969 B1 * | 7/2002 | Bertagna | 138/30 |
| 2003/0111473 A1 | 6/2003 | Carter et al. | 220/586 |

FOREIGN PATENT DOCUMENTS

| | | |
|---|---|---|
| DE | 4302356 | 8/1994 |
| DE | 19504750 | 8/1996 |
| DE | 19701577 | 7/1997 |
| NL | 8100723 | 9/1982 |
| WO | WO 02/39007 | 5/2002 |

OTHER PUBLICATIONS

Installation Instruction Sheet, Model 60TA5-1, Tank-E-Liminators, Webtrol, Weber Industries, Inc., dated before Jul. 24, 2003 (1 pg.).

Watts Industries, Inc., Series ILT-5 and ILT-12 In-Line Water Expansion Tanks, dated 2001 (2 pgs.).

International Search Report PCT/US 03/23170, 3pgs.

* cited by examiner

IN-LINE FLOW THROUGH DIAPHRAGM TANK

CROSS-REFERENCE TO RELATED APPLICATIONS

This application is a continuation-in-part of and claims the priority of U.S. patent application Ser. No. 10/281,708, filed Oct. 28, 2002, now abandoned and claims the priority of U.S. Provisional Application No. 60/398,765, filed Jul. 25, 2002, the entire contents of both of which are incorporated herein by reference.

FIELD OF THE INVENTION

The invention pertains to a diaphragm tank, and more specifically, to a flow-through diaphragm tank having robust construction.

BACKGROUND OF THE INVENTION

There are many settings within water delivery systems in which the amount of water that must be contained varies over time. For example, water expands when heated. In a closed system, this expansion may cause dangerous increases in water pressure. While water heaters have relief valves to vent excess pressure and prevent damage to the water heater and surrounding piping, it is undesirable to have hot water venting out of a tank in a residential setting. As a result, expansion tanks are used to absorb the excess pressure and release water back into the water heater when the pressure decreases. In addition, expansion tanks may be used to modulate pressure spikes in water systems in which pressure is supplied by a pump, e.g., domestic well systems. Expansion tanks also find applications in forced hot water heating systems, water towers, and other settings.

SUMMARY OF THE INVENTION

In one aspect, the invention is an in-line diaphragm tank including a case having first and second passage fittings providing fluidic communication between an exterior and an interior of the case, first and second collars sealingly connected to the first and second passage fittings, a resilient diaphragm having first and second ends sealingly connected to an exterior of the first and second collars, respectively, and a tube retained between the first and second collars and having two ends. One or both ends of the tube have a notch providing fluidic communication between an interior of the tube and an interior of the diaphragm. The case may be metallic and may include a shell having first and second ends and first and second domes welded to the first and second ends of the shell, respectively. The passage fittings may each be disposed in a wall of a dome. The tank may further include a valve providing controllable fluidic communication between an exterior of the tank and a space between the case and the diaphragm. The valve may be disposed in a wall of one of the domes or of the shell.

A cross-sectional area of the first and second ends of the diaphragm may be smaller than a cross-sectional area of a middle portion of the diaphragm. One or both ends of the tube may have a plurality of notches. A middle portion of the diaphragm may be configured to contact the tube at normal operating pressures. A portion of at least one of the collars may have an outer diameter that is approximately equal to an inner diameter of the diaphragm. The diaphragm may have a substantially uniform diameter along the length of the diaphragm. The diaphragm's diameter may be greater in size than a diameter of the tube.

In another aspect, the invention is an in-line diaphragm tank including a pressure assembly having an inlet and an outlet, a flow-through assembly having an interior and an exterior and first and second ends sealingly connected to the inlet and outlet, respectively, and a resilient diaphragm having a middle portion and first and second ends sealingly connected to the flow-through assembly. The cross-sectional area of the first and second ends of the diaphragm are smaller than a cross-sectional area of the middle portion, and a space between the exterior of the flow-through assembly and the interior of the diaphragm is in fluidic communication with the interior of the flow-through assembly. A space between the exterior of the flow-through assembly and the interior of the diaphragm may be in fluidic communication with the interior of the flow-through assembly. The flow-through assembly may include first and second collars sealingly connected to the inlet and outlet, respectively, and a tube retained between the first and second collars and having two ends. One or both ends of the tube may have a notch providing fluidic communication between an interior of the tube and an interior of the diaphragm.

In another aspect, the invention is an in-line diaphragm tank including a metallic pressure assembly, a flow-through assembly having an interior and an exterior, and a resilient diaphragm having inlet and outlet ends sealingly connected to the flow-through assembly. A space between the exterior of the flow-through assembly and an interior of the diaphragm are in fluidic communication. The pressure assembly includes first and second domes welded to the first and second ends of the shell, respectively, and first and second fittings attached to the first and second domes, respectively, and adapted and constructed for connection to a plumbing system and providing fluidic communication between an interior and an exterior of the case. First and second ends of the flow-through assembly are sealingly connected to the first and second fittings of the case, respectively.

In another aspect, the invention is a pre-assembled water chamber assembly for an expansion tank including a tube having first and second ends, first and second collars disposed at the first and second ends of the tube, respectively, and a resilient diaphragm having first and second ends. The diaphragm is disposed about the tube and the first and second ends of the diaphragm are sealingly fitted around the first and second collars, respectively.

BRIEF DESCRIPTION OF THE DRAWING

The invention is described with reference to the several figures of the drawing, in which.

DETAILED DESCRIPTION OF CERTAIN PREFERRED EMBODIMENTS

Figure 1A:
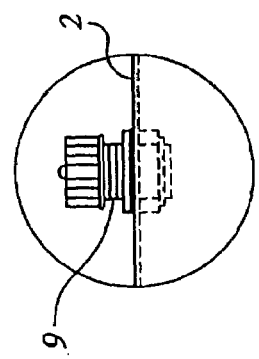
FIG. 1A is an exploded view of a valve body illustrated in FIG. 1.
Figure 1:
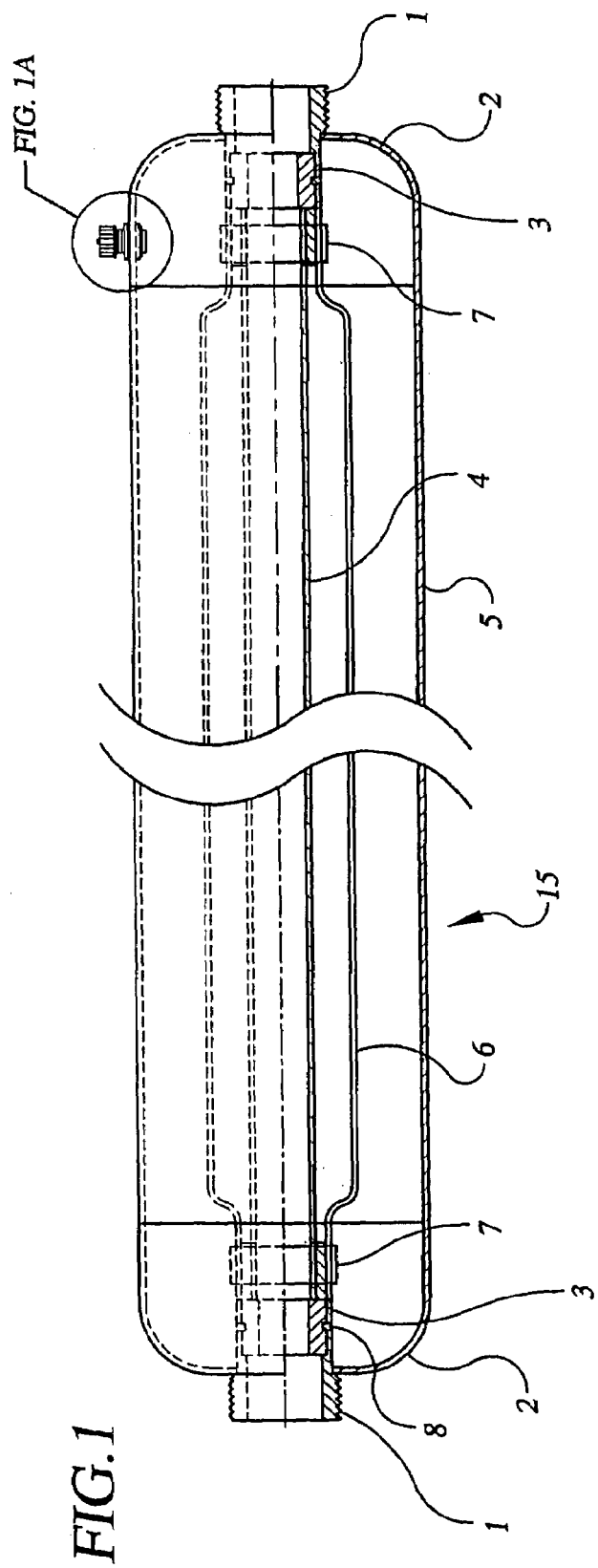
FIG. 1 is a schematic diagram of an in-line flow through diaphragm tank according to an embodiment of the invention.
Figure 3:
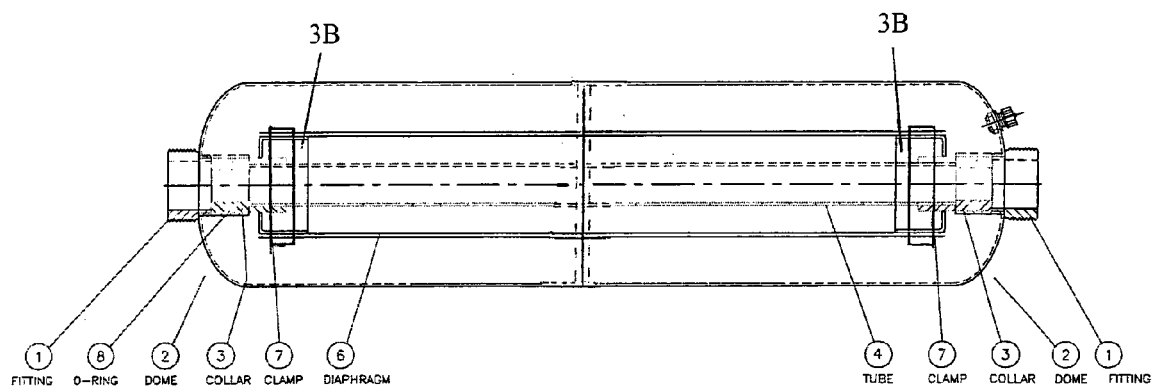
FIG. 3 is a schematic diagram of an alternative embodiment of the flow-through diagram tank illustrated in FIG. 1.

FIG. 1 illustrates a flow-through diaphragm tank 10 according to an embodiment of the invention. The tank 10 includes an external case, for example, pressure assembly 15, and an interior assembly via which water or other liquids flow through the tank 10, for example, water chamber assembly 12. The pressure assembly 15 may include a shell 5 that is capped at each end by domes 2. Alternatively, domes 2 may be elongated and may be attached, for example, through welding, to one another to form pressure assembly 15 (FIG. 3).

One skilled in the art will recognize that domes 2 may take on any shape so long as they may be attached to shell 5 or to each other, depending on the desired embodiment. For example, domes 2 may be cup-shaped, as shown, or flat caps with squared or rounded corners, or some other shape. Whether the pressure assembly 15 is formed from two domes 2 or two domes 2 and shell 5 depends partially on the size of the pressure assembly and the ease of forming domes 2 of the proper size. For example, if domes 2 are pressed from sheet metal, the walls of the pressure assembly 15 will be thinner as the domes 2 are pressed to greater lengths. The required thickness of the walls will depend on the pressure within the pressure assembly 15 during operation and may be easily determined by one skilled in the art.

It is preferable that the domes not flex significantly as the pressure within pressure assembly 15 changes. One of the domes 2 may be fitted with a valve body 9 through which the interior of pressure assembly 15 may be charged with air or vented. (FIG. 1A). Alternatively, valve body 9 may be disposed in shell 5. Under normal pressures, that is, when the pressure within the system is less than or equal to the precharge pressure within the tank (the pressure of the air between the pressure assembly 15 and the diaphragm when there is no water in the tank), water flows through the tank 10 by entering at one fitting 1, flowing through water chamber assembly 12, and exiting the tank 10 at the second fitting 1.

Figure 2:
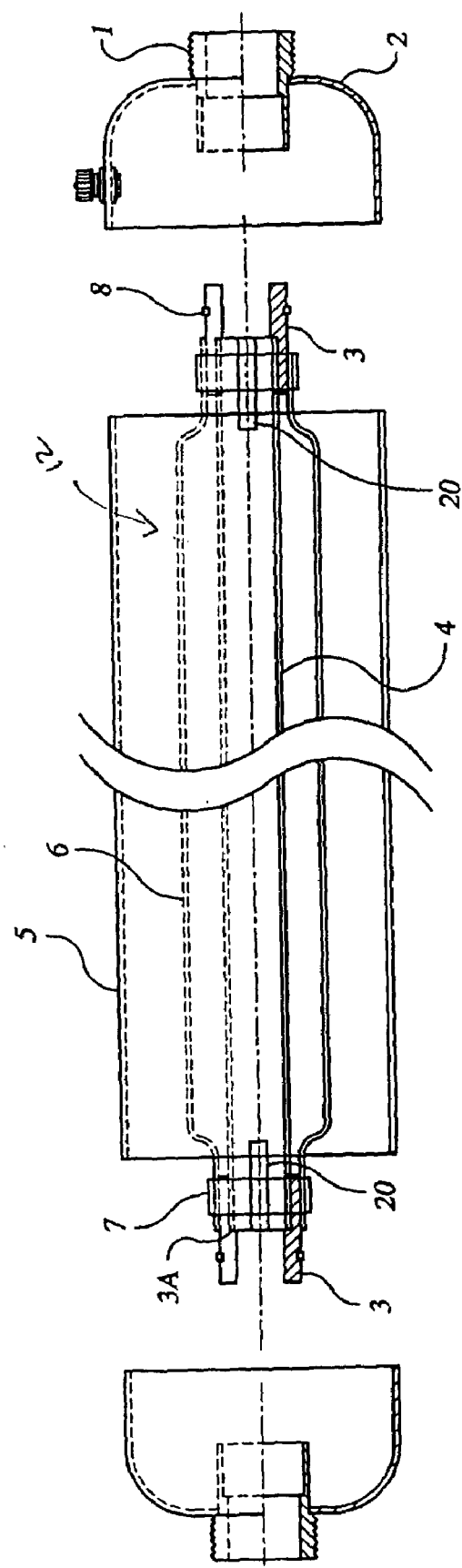
FIG. 2 is an exploded view of the diaphragm tank illustrated in FIG. 1.

An exploded view of the tank 10, isolating water chamber assembly 12, is shown in FIG. 2. The ends of tube 4 are inserted into collars 3 to form flow-through assembly 13. In one embodiment, each collar 3 has a shoulder 3A to prevent lateral motion of tube 4 within the collar 3. Water chamber assembly 12 is formed by affixing diaphragm 6 to flow-through assembly 13. Diaphragm 6 fits around the outside of collar 3 and is retained in place by clamps 7. Clamp 7 also prevents water leakage from water chamber assembly 12 to the space between the diaphragm 6 and pressure assembly 15. In the embodiment shown in FIG. 1, the ends of diaphragm 6 are tapered to reduce stress on the ends of the diaphragm 6 as it expands away from tube 4 (see below).

In an alternative embodiment, shown in FIG. 3, diaphragm 6 is straight, namely having a substantially uniform diameter along the entire length of the diaphragm. In this embodiment, collar 3 includes retainer 3B, whose outer diameter is approximately the same as the inner diameter of diaphragm 6. The retainer 3B may be formed on collar 3 as a monolithic piece, or the narrower portion of collar 3 may be formed separately and welded to retainer 3B. The diaphragm is then sealed to retainer 3B by clamp 7. One skilled in the art will recognize that the uniform diameter diaphragm may be used with a pressure assembly 15 having a shell 5 and two domes 2 or one formed with two domes 2 welded together.

To assemble the tank 10 as shown in FIG. 1, the water chamber assembly 12 is passed through outer shell 5. The ends of collars 3 are inserted into fittings 1. O-rings 8 in grooves in collar 3 prevent leakage of water from fitting 1 to the space between diaphragm 6 and pressure assembly 15. In one embodiment, the fittings 1 are already attached to domes 2. For example, the assembly of fitting 1 and domes 2 may be assembled as a monolithic piece. Alternatively, fittings 1 may be welded to domes 2. When the collars 3 are inserted into fittings 1, the tank 10 is essentially assembled. The domes 2 are sealingly secured to outer shell 5, preferably by welding, to form pressure assembly 15. One skilled in the art will recognize that one dome 2 may be welded to shell 5 before inserting water chamber assembly 12. As noted above, in an alternative embodiment, shell 5 is omitted and the two domes 2 are welded to one another.

Welding techniques such as metal-inert gas (MIG) and tungsten-inert gas (TIG) may be used to join the domes 2 to each other or to outer shell 5. Those skilled in the art will recognize that a variety of welding techniques may be used to join the various parts of pressure assembly 15. Because the joints are welded, an increase in pressure within the space between diaphragm 6 and pressure assembly 15 will not force the various parts of pressure assembly 15 to separate from one another.

As noted above, at normal operating pressures, water simply flows from one end of the tank 10 to the other through tube 4. At normal operating pressures, the space between pressure assembly 15 and diaphragm 6 is pressurized so that the diaphragm is pushed against the outer wall of tube 4. If the water pressure within the tube 4 exceeds the pressure between diaphragm 6 and shell 5, then water will flow into the space between tube 4 and diaphragm 6 through notches 20 cut into the ends of tube 4. In one embodiment, each end of tube 4 includes two notches 20, offset by 180 degrees. One skilled in the art will realize that more slots may be included if desired. For example, four slots with an offset of 90 degrees may be included. When the water pressure within tube 4 decreases, the diaphragm 6 is forced back against the outside of tube 4, pushing the water back into the tube from the space between tube 4 and diaphragm 6 through the notches 20.

EXAMPLE 1

Hot Water Heating

Figure 4:
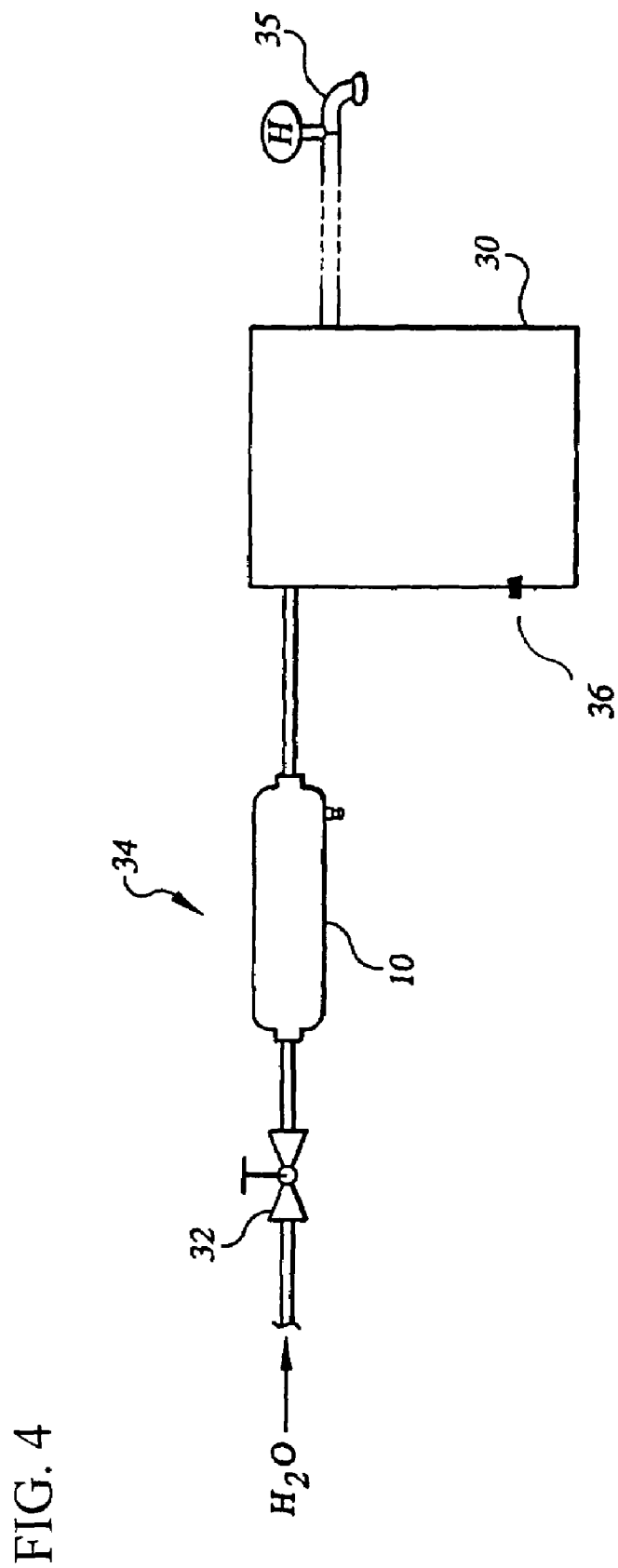
FIG. 4 is a schematic diagram of a portion of an exemplary plumbing system including a diaphragm tank according to an embodiment of the invention.

The tank 10 absorbs the increase in pressure from thermal expansion as water is heated in a hot water heater 30 (FIG. 4) for use by an enduser (e.g., in an open system). Such a system is called an open system because it supplies water to a user rather than continuously recycling the same water. A check valve 32 prevents the water from flowing back down supply side 34 from the heater 30. As water is heated in hot water heater 30, it expands. If there is no demand for the hot water (e.g., faucet 35 is closed), then the expanding water increases the pressure downstream of valve 32. While hot water heaters have pressure valves 36 to vent water and prevent damage to the heater, a homeowner is not likely to appreciate the safety advantages of having hot water venting out of the heater 30 into the rest of the home. To relieve the pressure, in-line tank 10 is disposed between the check valve 32 and the hot water heater 30 on the supply side 34 (cold water side) of the heater 30. As water heats up, its expansion increases the upstream water pressure, and the diaphragm expands. In one embodiment, the pressure between pressure assembly 15 and diaphragm 6 is at least 5 psi. One skilled in the art will recognize that the appropriate pressure will depend on the capacity of the water heater, the diameter of the piping, and the total capacity of the system.

A typical tank for such a system has a pressure assembly 15 of 1 gallon or more. On some systems, the volume of water may dictate volumes as great as 100 gallons or more. Because the tank is being used to hold potable water, it is important (and may be required by local building codes) that the water in the tank completely circulate through after sufficient downstream demand. Because water enters the diaphragm through the notches 20 at one end and leaves through the notches 20 at the other end, water passes through the tank on a FIFO (first-in, first-out) basis in the direction of flow through the tube 4. That is, given two portions of water entering the space between the diaphragm and the tube, substantially all of the first portion exits the tank before a substantial amount of the second portion exits the tank, even though the second portion may enter the space before a substantial amount of the first portion leaves the tank.

Figure 5:
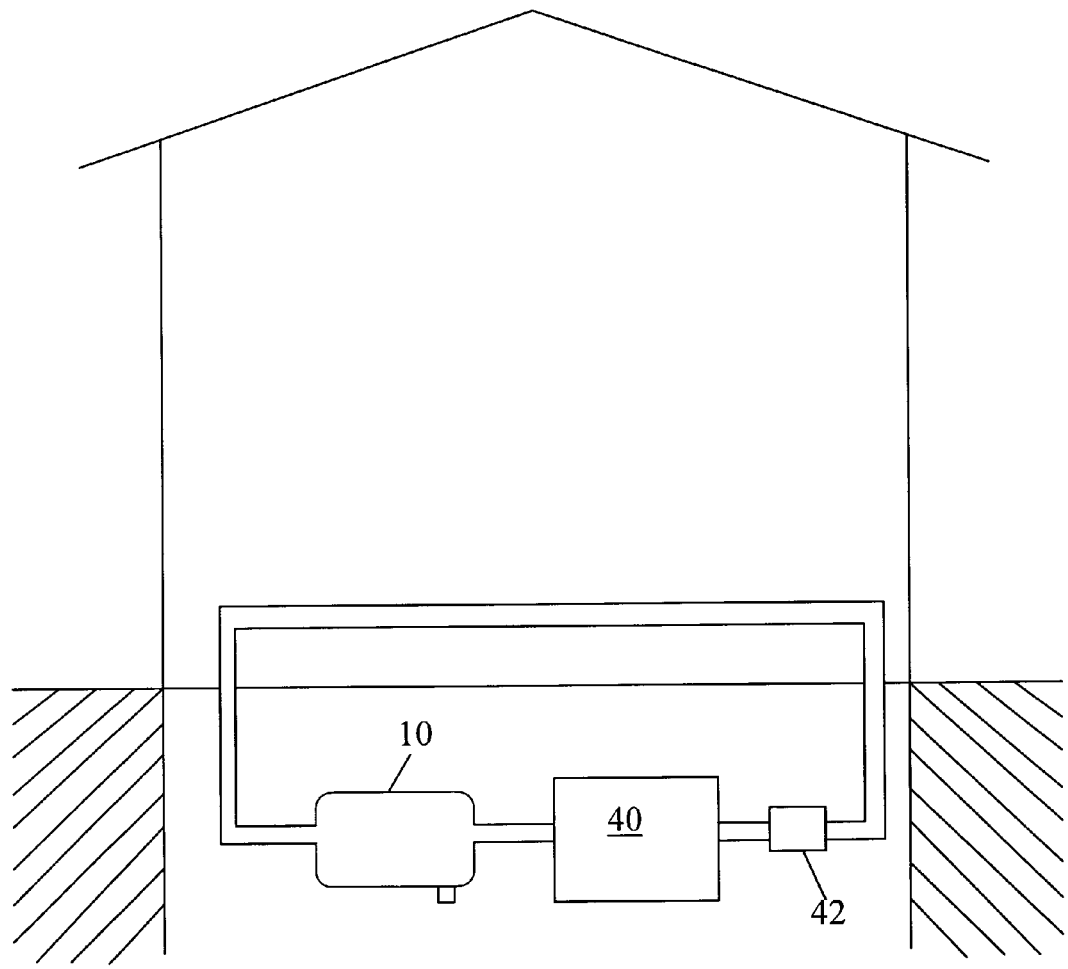
FIG. 5 is a schematic diagram of portion of an exemplary heating system including a boiler and diaphragm tank according to an embodiment of the invention.

A similar configuration may be employed to exploit the in-line tank 10 for use with a closed loop system, e.g., a forced hot water heating system for a home or other building. Tank 10 is installed upstream of boiler 40 (FIG. 5). When the circulator 42 is on, water from the tank 10 leaves the diaphragm and is circulated through the heating system. If the circulator is off but the boiler is on, the pressure of the expanding water is relieved by expansion of the diaphragm.

For either of these systems, the size and precharge setting of the diaphragm tank will depend on the volume of water being heated and the setting of the pressure relief valve. Typically, the precharged pressure of the tank, that is, the pressure between the uninflated diaphragm and the pressure assembly 15, is the same as the supply pressure for the system. For example, a 100 kbtu boiler may be used in combination with a 18 liter tank charged to 12 psi. The supply pressure for a boiler for a hot water heating/radiator system is typically between 10 and 30 psi; that for hot (potable) water heating may be much higher, as is known to those skilled in the art.

EXAMPLE 2

Well Systems

Figure 6:
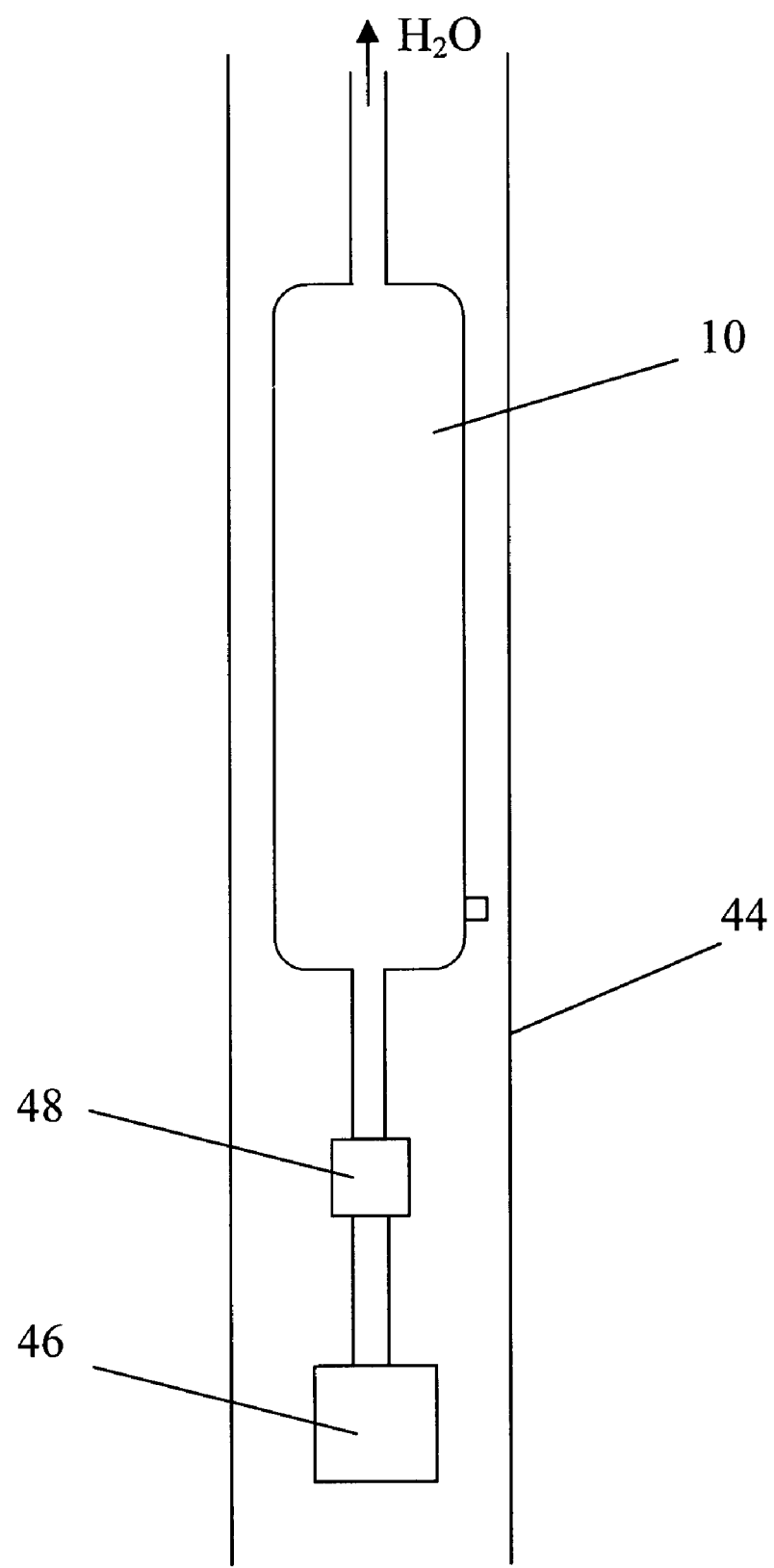
FIG. 6 is a schematic diagram of a portion of an exemplary well system including a pump and diaphragm tank according to an embodiment of the invention

The diaphragm tank 10 is inserted in well casing 44, downstream of pump 46 (FIG. 6). The tank satisfies small demands from a downstream user without engaging the pump. When the pump is on, water flows through both tube 4 and the space between tube 4 and diaphragm 6. Water flows from one end of the space to the other, ensuring that water enters and leaves the tank on a first-in-first-out basis. Typical tank systems for in-well systems have capacities between 1.5 and 5 gal, for example, 1.5, 3.1 and 4.5 gal. The primary limitation on the size of the tank is the diameter of the well; however, the volume may be increased by lengthening the tank 10.

To prevent pressure spikes in the tank, the rate at which the diaphragm expands should be controlled. One method of accomplishing this is to use a variable speed pump. The speed of the pump increases gradually, slowing increasing the flow and the pressure of water within the tank. Another method is to install a pressure regulating valve 48 between the pump 46 and tank 10. The valve moderates the rate of pressure increase downstream when the pump comes on.

The tank itself also moderates changes in pressure due to changes in demand. For example, when demand ceases, e.g., a faucet is turned off, the pump does not immediately slow down or stop. Water continues to be pumped into the plumbing system with no outlet, increasing the pressure. Some of this water passes into the space between the tube 4 and diaphragm 6, reducing the rate of pressure increase by effectively increasing the volume of the system. Conversely, the pump comes on after a user has already decreased the pressure in the system by running a faucet because it is the decrease in pressure that causes the pump to come on. The tank prevents pressure spikes due to the increase in pressure from the operation of the pump.

The lowest cut-in pressure for the pump is typically 20 psi; the highest cut-out pressure is typically about 100 psi. Typical pressure switches operate on a 20 psi differential between the cut-in and cut-out pressures. The desired pressure will depend on the equipment being supplied downstream of the tank. The piping and the pump should be able to support the desired pressures; likewise, tank 10 must be sufficiently robust to withstand the pressures within the system. One skilled in the art will recognize that the thickness of the diaphragm, outer shell, and dome materials, as well as the materials themselves, may be selected with the operating conditions in mind.

As for the water heating systems described in Example 1, the tank 10 ensures that water is delivered to an end user on a FIFO basis rather than a LIFO basis. Because the pump is pushing water upwards, the use of a variable speed pump or a pressure regulating valve provide the potential for water to stagnate in the delivery system. The tank 10 minimizes the residence time of water between the well and the user.

EXAMPLE 3

Anti-Hammer

The tank may also be used to reduce knocking, or hammering, in water systems that also contain air. For example, a water tower includes a drop pipe that occasionally requires emptying and clearing. When the pipe is refilled from the elevated tank, the falling water rapidly compresses the column of air in the pipe. The pressure from the falling water, which is accelerating under the force of gravity, is greater than the pressure exerted once the pipe is full, and the compressed air re-expands against the water. This expansion results in knocking in the pipes. Besides being noisy, it also strains pipe material, possibly weakening the pipe.

Indeed, in any large pipeline with water, the velocity of the water is great enough that potential energy from compression of air trapped within the line will cause hammering. A pressure tank can absorb the potential energy to prevent hammers. As for the water tower, the excess pressure at the point of the hammer strains the pipeline material. Repeated hammering will fatigue the pipe material, facilitating crack generation and propagation and eventual failure.

Tanks used in anti-hammer applications should be able to withstand pressures of 400–500 lbs or more. Those skilled in the art will be able to choose the dimensions of the various portions of the tank, including the total volume, wall thickness, diaphragm thickness, precharge pressure, etc., depending on the expected pressures within the completed system. These tanks may be exploited for both hydraulic (open) and hydronic (closed-loop) systems.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A in-line expansion tank, comprising:
a pressure assembly having first and second passage fittings providing fluidic communication between an interior and an exterior of the pressure assembly;
first and second collars sealingly connected to the first and second passage fittings, respectively;
a resilient diaphragm having first and second ends, wherein the first and second ends are sealingly connected to an exterior of the first and second collars, respectively; and
a tube retained between the first and second collars and having first and second ends, wherein both ends have a notch providing fluidic communication between an interior of the tube and an interior of the diaphragm, wherein the notch is open to the end of the tube,
wherein, when a first portion of water and a second portion of water enter the space, between the diaphragm and the tube at the first end of the tube, the second portion entering the space before a substantial amount of the first portion leaves the tank via the second end of the tube, substantially all of the first portion exits the tank before a substantial amount of the second portion exits the tank via the second end of the tube.

2. The in-line expansion tank of claim 1, further comprising a valve providing controllable fluidic communication between an exterior of the tank and a space between the pressure assembly and the diaphragm.

3. The in-line expansion tank of claim 2, wherein the pressure assembly is metallic and comprises a shell having first and second ends and first and second domes welded to the first and second ends of the shell, respectively, wherein the first and second passage fittings are disposed in a wall of the first and second domes, respectively, and wherein the valve is disposed in a wall of one of the domes or of the shell.

4. The in-line expansion tank of claim 2, wherein the pressure assembly is metallic and comprises first and second domes welded to one another, wherein the first and second passage fittings are disposed in a wall of the first and second domes, respectively, and wherein the valve is disposed in a wall of one of the domes.

5. The in-line expansion tank of claim 1, wherein a cross-sectional area of the first and second ends of the diaphragm is smaller than a cross-sectional area of a middle portion of the diaphragm.

6. The in-line expansion tank of claim 1, wherein a portion of at least one of said collars has an outer diameter that is approximately equal to an inner diameter of said diaphragm.

7. The in-line expansion tank of claim 1, wherein one or both of the ends of the tube have a plurality of notches.

8. The in-line expansion tank of claim 1, wherein at least a middle portion of the diaphragm is configured to contact the tube at normal operating pressures.

9. An in-line expansion tank, comprising:
a pressure assembly having an inlet and an outlet;
a flow-through assembly having an interior and an exterior and first and second ends sealingly connected to the inlet and outlet, respectively; and
a resilient diaphragm having a middle portion and first and second ends sealingly connected to the flow-through assembly, wherein
the interior diameter of the first and second ends of the diaphragm are smaller than the interior diameter of the middle portion, and
a space between the exterior of the flow-through assembly and the interior of the diaphragm is in fluidic communication with the interior of the flow-through assembly, wherein the flow-through assembly comprises:
first and second collars sealingly connected to the inlet and outlet, respectively; and
a tube retained between the first and second collars and having first and second ends, wherein both ends have a notch providing fluidic communication between an interior of the tube and an interior of the diaphragm, wherein the notch is open to the end of the tube,
wherein, when a first portion of water and a second portion of water enter the space, between the diaphragm and the tube at the first end of the tube, the second portion entering the space before a substantial amount of the first portion leaves the tank via the second end of the tube, substantially all of the first portion exits the tank before a substantial amount of the second portion exits the tank via the second end of the tube.

10. The in-line expansion tank of claim 9, wherein the pressure assembly is metallic and comprises a shell having two ends and first and second domes welded to the shell, wherein the inlet and the outlet each comprise a passage fitting disposed in a wall of one of the domes.

11. The in-line expansion tank of claim 10, further comprising a valve providing controllable fluidic communication between an exterior of the tank and a space between the pressure assembly and the diaphragm, wherein the valve is disposed in a wall of the shell or of one of the domes.

12. The in-line expansion tank of claim 9, wherein the pressure assembly is metallic and comprises first and second domes welded to one another, wherein the inlet and the outlet each comprise a passage fitting disposed in a wall of one of the domes.

13. The in-line expansion tank of claim 12, further comprising a valve providing controllable fluidic communication between an exterior of the tank and a space between the pressure assembly and the diaphragm, wherein the valve is disposed in a wall of one of the domes.

14. The in-line expansion tank of claim 9, wherein at least a middle portion of the diaphragm is configured to contact the tube at normal operating pressures.

15. The in-line expansion tank of claim 14, wherein one or both of the ends of the tube have a plurality of notches.

16. An in-line expansion tank, comprising:
a metallic pressure assembly, comprising:
first and second domes joined to form a chamber by a welded joint; and
first and second fittings attached to the first and second domes, respectively, and adapted and constructed for connection to a plumbing system and providing fluidic communication between an interior and an exterior of the pressure assembly;
a flow-through assembly having an interior and an exterior and first and second ends sealingly connected to the first and second fittings, respectively wherein the flow-through assembly comprises first and second collars sealingly connected to the first and second domes, respectively and a tube retained between the first and second collars and having two ends, wherein both ends have a notch providing fluidic communication between an interior of the tube and an interior of the diaphragm, wherein the notch is open to the end of the tube; and a resilient diaphragm having inlet and outlet ends sealingly connected to the flow-through assembly, wherein a space between the exterior of the flow-through assembly and the interior of the diaphragm are in fluidic communication, wherein, when a first portion of water and a second portion of water enter the space, between the diaphragm and the flow-through assembly via the inlet end the second portion entering the space before a substantial amount of the first portion leaves the tank via the outlet end, substantially all of the first portion exits the tank before a substantial amount of the second portion exits the tank via the outlet end.

17. The in-line expansion tank of claim 16, further comprising a valve providing controllable fluidic communication between an exterior of the tank and a space between the metallic pressure assembly and the diaphragm, wherein the valve is disposed in a wall of one of the domes.

18. The in-line expansion tank of claim 16, further comprising a shell having first and second ends, wherein the first and second domes are welded to the first and second ends of the shell to form the chamber.

19. The in-line expansion tank of claim 17, further comprising a valve providing controllable fluidic communication between an exterior of the tank and a space between the metallic pressure assembly and the diaphragm, wherein the valve is disposed in a wall of the shell or of one of the domes.

20. The in-line expansion tank of claim 16, wherein one or both of the ends of the tube have a plurality of notches.

21. The in-line expansion tank of claim 16, wherein a cross-sectional area of the first and second ends of the diaphragm is smaller than a cross-sectional area of a middle portion of the diaphragm.

22. The in-line expansion tank of claim 16, wherein a portion of at least one of said collars has an outer diameter that is approximately equal to an inner diameter of said diaphragm.

23. The in-line expansion tank of claim 16, wherein a diameter of the diaphragm is substantially uniform along the diaphragm's length and greater than a diameter of the tube.

24. The in-line expansion tank of claim 16, wherein at least a middle portion of the diaphragm is configured to contact the tube at normal operating pressures.

25. A preassembled water chamber assembly for an expansion tank, comprising:

a tube having first and second ends, each end having a notch open to the end of the tube;

first and second collars disposed at the first and second ends of the tube, respectively; and a resilient diaphragm having first and second ends, the diaphragm disposed about the tube and the first and second ends of the diaphragm sealingly fitted around the first and second collars, respectively, wherein, when a first portion of water and a second portion of water enter the space , between the diaphragm and the tube at the first end of the tube, the second portion entering the space before a substantial amount of the first portion leaves the tank via the second end of the tube, substantially all of the first portion exits the tank before a substantial amount of the second portion exits the tank via the second end of the tube.

26. The water chamber assembly of claim 25, wherein a cross-sectional area of the first and second ends of the diaphragm is smaller than a cross-sectional area of a middle portion of the diaphragm.

27. The water chamber assembly of claim 25, wherein a portion of at least one of said collars has an outer diameter that is approximately equal to an inner diameter of said diaphragm.

28. The water chamber assembly of claim 25, wherein one or both of the ends of the tube have a plurality of notches.

* * * * *